(12) United States Patent
Boden et al.

(10) Patent No.: US 10,343,385 B2
(45) Date of Patent: Jul. 9, 2019

(54) BODILY IMPLANT

(71) Applicant: Boston Scientific Scimed, Inc., Maple Grove, MN (US)

(72) Inventors: Mark W. Boden, Harrisville, RI (US); Kasyap Seethamraju, Eden Prairie, MN (US); Eric Michael Petersen, Maple Grove, MN (US); Sandra Nagale, Lowell, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 316 days.

(21) Appl. No.: 14/332,100

(22) Filed: Jul. 15, 2014

(65) Prior Publication Data
US 2015/0025308 A1 Jan. 22, 2015

Related U.S. Application Data

(60) Provisional application No. 61/847,660, filed on Jul. 18, 2013.

(51) Int. Cl.
*A61F 2/00* (2006.01)
*B32B 38/00* (2006.01)
(Continued)

(52) U.S. Cl.
CPC ...... *B32B 38/0012* (2013.01); *A61B 17/0469* (2013.01); *A61F 2/0045* (2013.01);
(Continued)

(58) Field of Classification Search
CPC ............... A61F 2/0045; A61F 2/0063; A61F 2002/0068
See application file for complete search history.

(56) References Cited

U.S. PATENT DOCUMENTS 6,042,534 A 3/2000 Gellman et al.
6,197,036 B1 * 3/2001 Tripp ............... A61F 2/0063
606/151

(Continued)

FOREIGN PATENT DOCUMENTS

WO 2002019945 A2 3/2002
WO 2006052695 A1 5/2006
(Continued)

OTHER PUBLICATIONS

Feola, et al., "Impact of Pregnancy and Vaginal Delivery on the Passive and Active Mechanics of the Rat Vagina", Ann Biomed Eng., vol. 39, Issue 1, Jan. 2011, pp. 549-558.
(Continued)

*Primary Examiner* — Catherine B Kuhlman
(74) *Attorney, Agent, or Firm* — Brake Hughes Bellermann LLP

(57) ABSTRACT

In one embodiment, an implant includes a body member, a first arm member and a second arm member. The body member is formed of a first material and has a first side portion and a second side portion. The body member has a first stiffness and includes multiple apertures through the body member. The first arm member is formed of a second material and is coupled to and extends from the body member. The second arm member is formed of the second material and is coupled to and extends from the body member. The first arm member and the second arm member have a second stiffness, the second stiffness being more than the first stiffness.

15 Claims, 6 Drawing Sheets

(51) Int. Cl.
    *A61B 17/04*     (2006.01)
    *A61B 17/062*    (2006.01)
    *A61B 17/00*     (2006.01)

(52) U.S. Cl.
    CPC . *A61B 17/0625* (2013.01); *A61B 2017/00805* (2013.01); *A61B 2017/047* (2013.01); *A61F 2250/0018* (2013.01); *Y10T 156/1002* (2015.01)

(56) References Cited

U.S. PATENT DOCUMENTS

| | | | |
|---|---|---|---|
| 7,824,462 B2 | 11/2010 | Webster | |
| 7,975,698 B2 | 7/2011 | Browning | |
| 8,506,582 B2 | 8/2013 | Kammerer | |
| 2003/0023137 A1 | 1/2003 | Gellman | |
| 2004/0059356 A1* | 3/2004 | Gingras | A61F 2/105 606/151 |
| 2004/0249473 A1* | 12/2004 | Delorme | A61B 17/06 623/23.64 |
| 2005/0043820 A1* | 2/2005 | Browning | A61F 2/0077 623/23.74 |
| 2006/0229493 A1* | 10/2006 | Weiser | A61B 17/00234 600/37 |
| 2007/0032695 A1 | 2/2007 | Weiser | |
| 2008/0177132 A1* | 7/2008 | Alinsod | A61F 2/0045 600/37 |
| 2008/0200751 A1* | 8/2008 | Browning | A61B 17/0401 600/30 |
| 2009/0005867 A1* | 1/2009 | Lefranc | A61F 2/0045 623/11.11 |
| 2009/0171142 A1* | 7/2009 | Chu | A61B 17/0401 600/37 |
| 2009/0171143 A1 | 7/2009 | Chu | |
| 2009/0171377 A1 | 7/2009 | Intoccia | |
| 2009/0221868 A1* | 9/2009 | Evans | A61F 2/0045 600/37 |
| 2009/0281558 A1 | 11/2009 | Li | |
| 2009/0281635 A1 | 11/2009 | Li | |
| 2010/0023104 A1 | 1/2010 | Desai | |
| 2010/0179298 A1 | 7/2010 | Faust | |
| 2010/0312043 A1* | 12/2010 | Goddard | A61F 2/0045 600/30 |
| 2011/0184228 A1 | 7/2011 | Sherry | |
| 2011/0245589 A1 | 10/2011 | Palma | |
| 2013/0178696 A1* | 7/2013 | Lotze | A61F 2/0045 600/37 |
| 2013/0204077 A1 | 8/2013 | Nagale | |
| 2013/0330688 A1 | 12/2013 | Hedrick | |

FOREIGN PATENT DOCUMENTS

| | | |
|---|---|---|
| WO | 2007014241 A1 | 2/2007 |
| WO | 2009158600 A1 | 12/2009 |
| WO | 2010052584 A2 | 5/2010 |
| WO | 2010093333 A1 | 8/2010 |

OTHER PUBLICATIONS

Lu, et al., "Improved endothelial cell adhesion and proliferation on patterned titanium surfaces with rationally designed, micrometer to nanometer features", Acta Biomateriala, vol. 4, Issue 1, Jan. 2008, pp. 192-201.

Pattison, et al., "Evaluating the In Vitro and In Vivo Efficacy of Nano-Structured Polymers for Bladder Tissue Replacement Applications", Macromolecular Bioscience, vol. 7, Issue 5, May 10, 2007, pp. 690-700.

Thapa, et al., "Nano-Structured polymers enhance bladder smooth muscle cell function", Biomaterials 24, 2003, pp. 2915-2926.

Whiteside, "Molecular engineering of surfaces using self-assembled monolayers", Sci. Prog. 88, 2005, pp. 17-48.

Duma, et al., "A Computational Model of the Pregnant Occupant: Effects of Restraint Usage and Occupant Position on Fetal Injury Risk", Paper No. 05-0367, 19th International Technical Conference on the Enhanced Safety of Vehicles, 2005, 9 pages.

Shahryarinejad, et al., "Effect of hormone replacement and selective estrogen receptor modulators (SERMs) on the biomechanics and biochemistry of pelvic support ligaments in the cynomolgus monkey (*Macaca fascicularis*)", Am J Obstet Gynecol, vol. 202, Issue 5, May 2010, pp. 485.e1-485.e9.

Non-Final Office Action for U.S. Appl. No. 13/762,131, dated Sep. 21, 2017, 24 pages.

* cited by examiner

BODILY IMPLANT

CROSS-REFERENCE TO RELATED APPLICATION

This application is a Nonprovisional of, and claims priority to, U.S. Patent Application No. 61/847,660, filed on Jul. 18, 2013, entitled "BODILY IMPLANT", which is incorporated by reference herein in its entirety.

TECHNICAL FIELD

This disclosure relates generally to medical devices and more particularly to implants configured to provide support within a body of a patient and methods for securing such implants with the body of the patient.

BACKGROUND

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways. For example, some implants are formed of a biologic material while others are formed or synthetic materials. Some biologic implants are known to breakdown within the body of the patient over time. Accordingly, in some cases, the patient can experience a recurrence of the dysfunction or prolapse condition. Some implants formed with synthetic materials may be more stable within the body of the patient, but may cause erosion of bodily tissue near the incision (for example, near the vaginal incision created to place the implant).

Accordingly, it is desirable to provide an implant that mimics the properties of the native tissue.

SUMMARY

In one embodiment, an implant includes a body member, a first arm member and a second arm member. The body member is formed of a first material and has a first side portion and a second side portion. The body member has a first stiffness and includes multiple apertures through the body member. The first arm member is formed of a second material and is coupled to and extends from the body member. The second arm member is formed of the second material and is coupled to and extends from the body member. The first arm member and the second arm member have a second stiffness, the second stiffness being more than the first stiffness.

In one embodiment, a method of forming an implant includes providing a polymer sheet, cutting a plurality of apertures in the polymer sheet and shaping the polymer sheet into a body member. The body member has a first stiffness and is to be disposed within a body of a patient and to provide support for a portion of the body of the patient. The method includes coupling a first arm member to the body member and coupling a second arm member to the body member, where the first arm member and the second arm member have a second stiffness and the second stiffness is more than the first stiffness.

DETAILED DESCRIPTION

Figure 1:
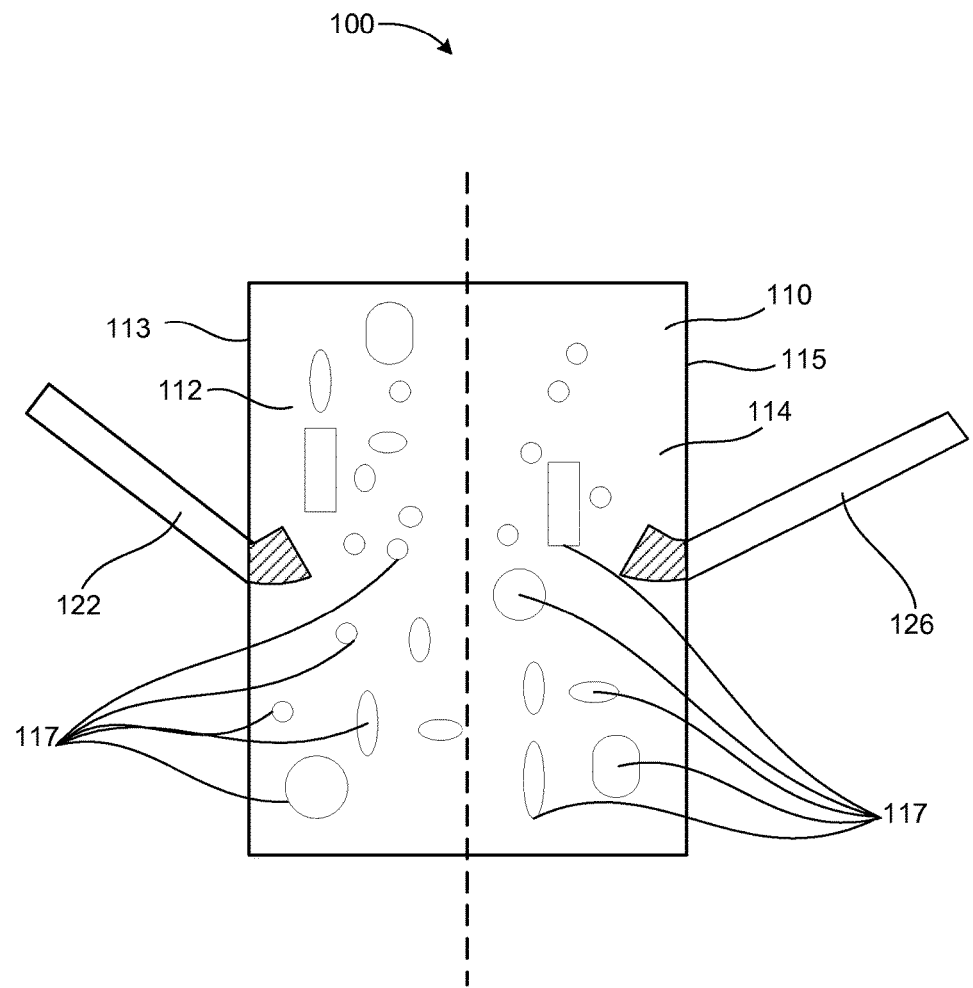
FIG. 1 is a schematic illustration of an implant according to an embodiment of the invention.

The devices and methods described herein are generally directed to implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different female pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures as desired. A procedure to deploy a pelvic implant can include vaginal incisions, such as an anterior vaginal incision and/or a posterior vaginal incision. In some embodiments, a procedure may include an exterior incision.

Various embodiments of implants are described herein. An implant can be delivered to a pelvic region of a patient using a variety of different delivery devices, only some examples of which are described herein. Various delivery aids are also described, some of which can be included as part of an implant (e.g., provided to a physician assembled) some of which can be assembled to an implant just prior to implantation. Such delivery aids are typically removed after placing one or more straps of an implant at a desired tissue securement location, leaving the strap to engage the tissue and support the support portion of the implant. For example, a sleeve or dilator assembly can be used to lead an implant or a strap of an implant through a tissue in an intracorporeal location (i.e., within the patient's body), such as the sacrospinous ligament or arcus tendineus. In other embodiments, a sleeve or dilator assembly can be used to lead an implant or a strap of an implant through a tissue and to an extracorporeal location (outside the patient's body), such as through an obturator membrane or muscle and out through an exterior incision in the patient.

In some embodiments, an implant can be associated to delivery aid, such as a sleeve assembly or dilator device, after such delivery aid has been placed within a pelvic region. For example, in an embodiment of an implant having multiple straps, prior placement of a delivery aid can help with coordinating and organizing the placement of the various straps. Placing a delivery aid within a pelvic region first also helps reduce handling of the implant which can reduce damage to the implant during an implantation procedure.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve assembly or dilator device as described herein refers to the end or portion of the device that is first inserted into a body of a patient during a medical procedure. The proximal end or portion is the end or portion of the device that is inserted into a body of the patient after the distal end or distal portion. The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that is inserted into the body after the leading end.

FIG. 1 is a schematic illustration of an implant 100 according to an embodiment. The implant 100 includes a body member 110, a first arm member 122 and a second arm member 126. The implant 100 is configured to be disposed within a body of a patient and to provide support to a portion of the body of the patient. For example, in some embodiments, the implant 100 is configured to be disposed within a pelvic region of a patient and is configured to provide support to a portion of the body of the patient (such as a bladder or a uterus of the patient).

In some embodiments, the implant 100 is configured to be disposed within the body of the patient such that the body member 110 is disposed adjacent to a portion of the body that is in need of support (such as a bladder or a uterus of the patient) and the first arm member 122 and the second arm member 126 are disposed within or coupled to bodily tissue to support the implant 100 within the body of the patient. For example, in some embodiments, the first arm member 122 and the second arm member 126 are configured to be disposed within or otherwise coupled to a ligament of a patient. While many of the embodiments of the implant described herein are described as being configured to be disposed within a female patient, in some embodiments, the implant is shaped and configured to be placed in a body of a male patient and is configured to provide support to a portion of a body of a male patient.

The body member 110 is formed of a first material and includes a first side portion 112 (having an edge 113) and a second side portion 114 (having an edge 115). The body member 110 may be of any size or shape suitable for the purpose of the implant. For example, for implants that are configured to support a bladder of a patient, the body member may be of one shape. The body member may be of a different shape in an implant that is configured to support a uterus or other portion of the body of the patient.

In some embodiments, the body member 110 is formed of an elastic polymer. For example, the body member 110 may be made of polypropylene, block copolymers (e.g., SIBS, SBS, PCT-b-PLA, etc.), polyurethanes, polyesters, poly(lactic acid), poly(lactide-co-glycolide), polycaprolactones, biosynthesized cellulose, and their copolymers. The body member 110 and its materials may have elastic and recoil properties that mimic the properties of the native tissue. In this manner, the body member 110 may include a stiffness or elasticity that is the same as or substantially similar to the stiffness or elasticity of the native tissue in the body of the patient. A stiffness property also may include and may refer to other related and/or similar properties interchangeably such as, for example, elasticity, compliance, flexibility, etc.

The elastic properties of the body member 110 may help to ensure favorable tissue ingrowth after implantation. The recoil properties of the body member 110 may help to ensure that the body member 110 maintains its original mechanical properties even after multiple stresses, which may originate from natural physical activity of the patient.

In some embodiments, the body member 110 made of an elastic polymer may include or be coated with one or more drugs (e.g., estrogen, progesterone, etc.) or proteins (e.g., collagen, elastin, etc.) for continuous delivery from the body member 110. In some embodiments, the body member 110 may include one or more antimicrobial compounds, or other coatings such as proteoglycans, which may interact with fibrin and collagen to form networks important to the function of the surrounding tissue.

In other embodiments, the body member 110 may be formed or made of a tissue engineering material containing micro-sized and/or nano-sized features or containing cells to enable appropriate cell growth and tissue incorporation. The body member 110 formed from tissue engineering material also may include a stiffness or elasticity that mimics the stiffness or elasticity of the bodily tissue that it is designed to support.

In one embodiment, the body member 110 has properties of the bodily tissue (e.g., vaginal tissue). For example, the body member 110 may have the same or nearly the same elastic modulus as vaginal tissue. The body member 110 includes properties such that the body member 110 may be able to withstand deformation after multiple stresses.

In one embodiment, the body member 110 is formed by a manufacturing process. For example, in one embodiment, the body member 110 is extruded using an extrusion process (e.g., polymer extrusion). In another embodiment, the body member is molded using a molding process (e.g., polymer molding). In another embodiment, the body member 110 is cast using a solution casting process (e.g., polymer solution casting).

In one embodiment, the body member 110 includes multiple apertures 117. The apertures 117 may be different sizes and/or different shapes and orientations. The apertures 117 may be holes through the body member 110. The apertures 117 may be sized and shaped and placed to achieve the desired stiffness and/or elastic properties of the body member 110 such that the properties of the body member mimic or match the properties, including the desired stiffness and/or elastic properties, of the bodily tissue. The size, shape, number and location of the apertures 117 may define the stiffness and/or elastic and/or other properties of the body member 110.

In one embodiment, the apertures 117 include various shapes having various aspect ratios to mimic the anisotropic properties of bodily tissue. In one embodiment, the body member 110 may be shaped similar to or the same as the shape of an Uphold™ Vaginal Support System by Boston Scientific Corporation. The body member 110 may be a flat sheet with apertures 117 having elastic properties of bodily tissue (e.g., vaginal tissue).

In one embodiment, the apertures 117 may be cut through a polymer sheet that has been provided (e.g., by polymer extrusion, polymer molding or polymer solution casting). For example, in one embodiment, the apertures 117 may be laser cut through a polymer sheet. The apertures 117 may be mm-sized holes. In other embodiments, other size holes may be laser cut. In another embodiment, the apertures may be dye cut through a polymer sheet, where the aperture are mm-sized holes. In other embodiments, other size holes may be dye cut.

In some embodiments, the apertures 117 may not penetrate all the way through the material. In these embodiments, one or more tools may be used to create grooves or divets or similar-type indentations in the body member 110, without penetrating all the way through the material. These type of apertures that do not go all the way through also may be used to obtain the desired properties of the body member 110. In other embodiments, the body member 110 may include a combination of different types of apertures, including apertures that penetrate through the material and apertures that do not penetrate through the material.

The first arm member 122 and the second arm member 126 are coupled to the body member 110. In one embodiment, the first arm member 122 and the second arm member 126 are not coupled together. Rather each of the first arm member 122 and the second arm member are individually coupled to the body member 110.

The first member 122 and the second arm member 126 may be of any size or shape suitable for the specific purpose of the implant. For example, for implants that are configured to support a bladder of a patient, the first arm member 122 and the second arm member 126 may be of one shape. The first arm member 122 and the second arm member 126 may be of a different shape in an implant that is configured to support a uterus or other portion of the body of the patient. For example, in some embodiments, the first arm member 122 and the second arm member 126 may be the same size and shape. In other embodiments, the first arm member 122 may be thicker or wider than the second arm member 126 or vice versa. In other embodiments, the first arm member 122 may be longer than the second arm member 126 or vice versa.

In some embodiments, the first arm member 122 and the second arm member 126 are formed from a second material. In some embodiments, the second material may be a same material as the first material that forms that body member 110. In other embodiments, the second material may be a different material than the first material that forms the body member 110.

In some embodiments, the first arm member 122 and the second arm member 126 are formed of an elastic polymer. For example, the first arm member 122 and the second arm member 126 may be made of polypropylene, block copolymers (e.g., SIBS, SBS, PCT-b-PLA, etc.), polyurethanes, polyesters, poly(lactic acid), poly(lactide-co-glycolide), polycaprolactones, biosynthesized cellulose, and their copolymers. The first arm member 122 and the second arm member 126 and their materials may have elastic and recoil properties that mimic the properties of the ligaments to which the first arm member 122 and second arm member 126 may be attached. In this manner, the first arm member 122 and the second arm member 126 may include a stiffness or elasticity that is the same as or substantially similar to the stiffness or elasticity of the ligaments in the body of the patient.

In other embodiments, the first arm member 122 and the second arm member 126 may be formed from knitted mesh, which may be produced using polymer filaments. In other embodiments, the first arm member 122 and the second arm member 126 may be formed or made of a tissue engineering material containing micro-sized and/or nano-sized features or containing cells to enable appropriate cell growth and tissue incorporation.

In one example embodiment, the first arm member 122, the second arm member 126 and the body member all may be formed from knitted mesh. A difference in properties, including stiffness properties, between the different members may be achieved by using different weaved patterns in the knitted mesh. For example, the arm members 122 and 126 may include one pattern in the knitted mesh material and the body member 110 may include a different pattern in the knitted mesh material, where the difference in patterns provides differences in properties that allow the different members to mimic the properties of different body parts.

In one embodiment, the first arm member 122 and the second arm member 126 may be made of flat material or substantially flat material. In other example embodiments, the first arm member 122 and the second arm member 126 are substantially flat. The properties of the first arm member 122 and the second arm member 126 may be different from the properties of the body member 110. For example, the first arm member 122 and the second arm member 126 may have different stiffness and/or elastic properties than the body member 110. The first arm member 122 and the second arm member 126 may be stiffer and/or less elastic than the body member 110. In this manner, the first arm member 122 and the second arm member 126 may mimic the properties of the ligaments to which they are attached and the body member 110 may mimic the properties of the tissue to which it supports. The stiffer first arm member 122 and the stiffer second arm member 126 may have mechanical properties that mimic those of the ligaments, including having a strength up to and including about 100 times the strength of the bodily tissue (e.g., vaginal tissue).

In the illustrated embodiment, the first arm member 122 and the second arm member 126 do not include any apertures. That is, there are no holes through the first arm member 122 and the second arm member 126. The lack of apertures in the first arm member 122 and the second arm member 126 may provide a difference in properties (e.g., stiffness and/or elastic properties) between the arm members 122 and 126 and the body member 110. In this manner, the arm members 122 and 126 without apertures may mimic the properties, including the strength properties, of the ligaments and the body member 110 with apertures 117 may mimic the properties of the bodily tissue (e.g., vaginal tissue).

In other example embodiments where the first arm member 122, the second arm member 126 and the body member 110 are made from the same material, a difference in stiffness properties between the arm members 122 and 126 and the body member 110 may be achieved by altering the properties of the material. For example, the material used to form the arm members 122 and 126 may be thicker than the same material used to form the body member 110 or vice versa. In other examples, reinforcement materials may be added to either the arm members 122 and 126 or the body member 110 to change the stiffness properties, including for example, fillers or fibers. Members have fibers or fillers added to the material may exhibit an increase in stiffness. In other examples, a coating may be added to the material to change the stiffness property of the material.

Figure 2:
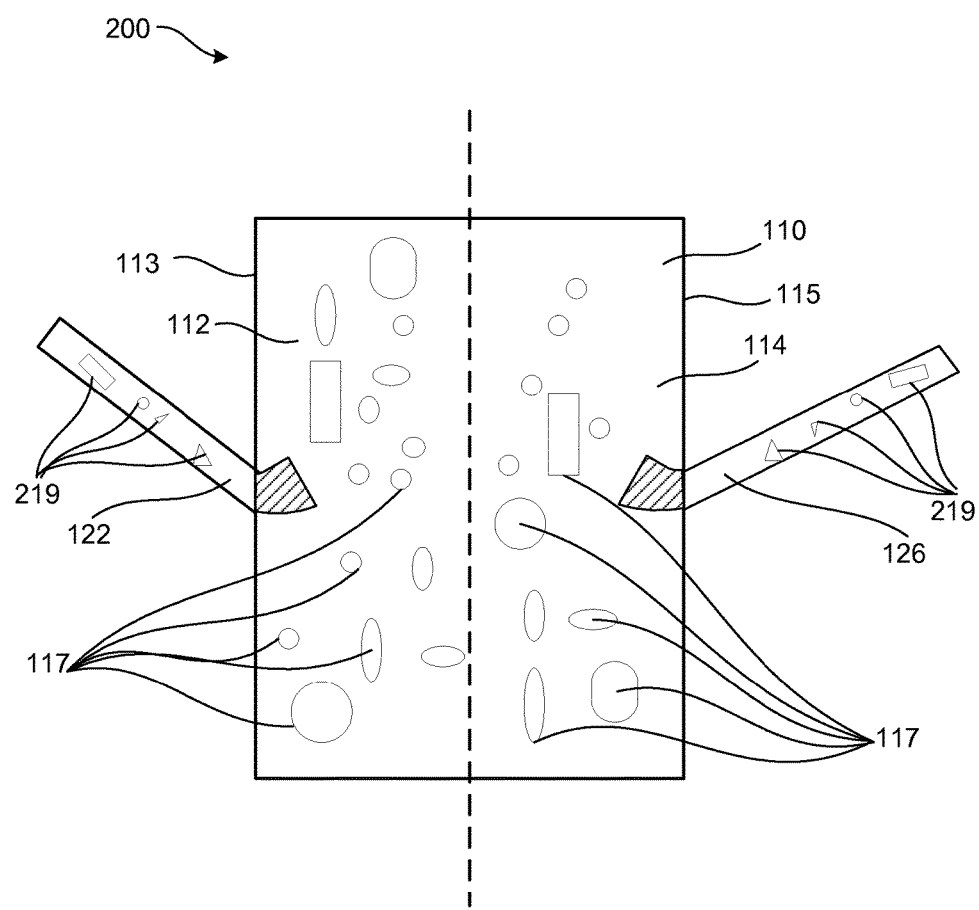
FIG. 2 is a schematic illustration of an implant according to an embodiment of the invention.

Referring to FIG. 2, another example embodiment of an implant 200 is illustrated. In the example embodiment, implant 200 may include the same or similar features as the implant 100 of FIG. 1 other than in this example embodiment, implant 200 includes a first arm member 122 and a second arm member 126 having apertures 219.

The apertures 219 may be different sizes and/or different shapes. The apertures 219 may be different sizes and/or different shapes from the apertures 117 formed through the body member 110. The apertures 219 may give the first arm member 122 and the second arm member 126 the desired properties that mimic the properties (e.g., stiffness and elasticity) of the ligaments to which the first arm member 122 and the second arm member 126 may be attached. The number, size, shape, location and/or orientation of the apertures 219 may achieve the desired properties in the first arm member 122 and the second arm member 124.

In one embodiment, the first arm member 122 and the second arm member 124 may be provided from the same polymer sheet as the body member 110 using the same polymer manufacturing processes discussed above. The apertures 219 may be cut through the first arm member 122 and the second arm member 126. For example, in one embodiment, the apertures 219 may be laser cut through the first arm member 122 and the second arm member 126. In another embodiment, the apertures 219 may be dye cut through the first arm member 122 and the second arm member 126.

In one embodiment, the apertures 219 may have different sizes and/or different shapes than the apertures 117. The difference in the aperture sizes and/or shapes may achieve the difference in properties between the body member 110 and the first arm member 122 and the second arm member 126, even if the body member 110 and the arm members 122 and 126 are integrally formed from the same polymer sheet.

In some embodiments, the apertures 117 may not penetrate all the way through the material. In these embodiments, one or more tools may be used to create grooves or divets or similar-type indentations in the arm members 122 and 126, without penetrating all the way through the material. These type of apertures that do not go all the way through also may be used to obtain the desired properties of the arm members 122 and 126. In other embodiments, the body member 110 may include a combination of different types of apertures, including apertures that penetrate through the material and apertures that do not penetrate through the material.

Referring also back to FIG. 1, the first arm member 122 extends from the first side portion 112 of the body member 110 in a first direction. The second arm member 126 extends from the second side portion 114 of the body member 110 in a second direction. In some embodiments, the second direction is different than the first direction. For example, in some embodiments, the second direction and the first direction are opposite directions. In other embodiments, the first direction and the second direction are different directions but are not opposite directions.

In some embodiments, the first arm member 122 and the second arm member 126 are substantially linear. In other embodiments, the first arm member 122 and the second arm member 126 include curved portions.

In some embodiments, the first arm member 122 and the second arm member 126 are coupled to the body member 110 such that a surface of the arm members 122 and 126 are disposed adjacent to a surface of the body member 110. In other words, the arm members 122 and 126 overlay or overlap a portion of the body member 110. For example, in the illustrated embodiment, the first arm member 122 and the second arm member 126 overlay or overlap a portion of the body member 110 between the edges 113 and 115, respectively, of the body member 110.

In some embodiments, the first arm member 122 and the second arm member 126 are coupled to the body member 110 on a same side. For example, the first arm member 122 and the second arm member 126 may extend from the first side portion 112 of the body member 110. In another example, the first arm member 122 and the second arm member 126 may extend from the second side portion 114 of the body member 110. In other example embodiments, more than two arm members may be coupled to the body member 110.

The first arm member 122 and the second arm member 126 may be coupled to the body member 110 using any known method. In some embodiments, the first arm member 122 and the second arm member 126 are coupled to the body member 110 via a suture. In other words, the first arm member 122 and second arm member 126 are sewn to or stitched to the body member 110. For example, in some embodiments, a sewing machine (or other type of machine) may be used to couple or sew the first arm member 122 and the second arm member 126 to the body member 110. In other embodiments, the first arm member 122 and the second arm member 126 are hand sewn to the body member 110. Any of a number of stitch patterns may be used to sew the first arm member 122 and the second arm member 126 to the body member 110. For example, a lock stitch, a zig zag stitch, or a custom stitch may be used. Additionally, any stitch density or thread size may be used to sew the first arm member 122 and the second arm member 126 to the body member 110.

In other embodiments, another method of coupling is used to couple the first arm member 122 and the second arm member 126 to the body member 110. For example, in some embodiments, a biocompatible adhesive is used to couple the first arm member 122 and the second arm member 126 to the body member 110. In other embodiments, a clip, such as a clip formed of polypropylene, a biocompatible staple, a rivet, or a button is used to couple the first arm member 122 and the second arm member 126 to the body member 110. In some embodiments, the first arm member 122 and the second arm member 126 are woven through openings defined by the body member 110 to couple the first arm member 122 and the second arm member 126 to the body member 110. In other embodiments, the first arm member 122 and the second arm member 126 may be heat welded to the body member 110.

Although only one extension member is illustrated, in some embodiments, the implant includes more than two arm members. For example, the implant 100 may include any number of arm members. In such embodiments, the arm members may extend to different portions within the body of the patient. For example, in some embodiments, two arm members may extend from the body member to the sacrospinous ligament of the patient and two arm members may extend from the body member to the arcus tendentious of the patient. Also, in some embodiments, the implant 100 may include a single arm member that extends from the body member.

In some embodiments, the first arm member 122 and the second arm member 126 include tangs or tanged portions that are configured to help retain the arm members in place within the bodily tissue in which they are disposed. The terms "tanged" or "tangs" as used herein mean roughened or jagged edges or areas, such as can result from cutting a woven or knit mesh material. In other embodiments, the first arm member 122 and the second arm member 126 include barbs, dimples and/or other protrusions configured to engage the bodily tissue of the patient to help retain the implant 100 in place within the body of the patient. In other embodiments, other mechanisms may be used to couple the first arm member 122 and the second arm member 126 to the bodily tissue. For example, in one embodiment the first arm member 122 and the second arm member 126 may be sewn with sutures to the bodily tissue.

Figure 4:
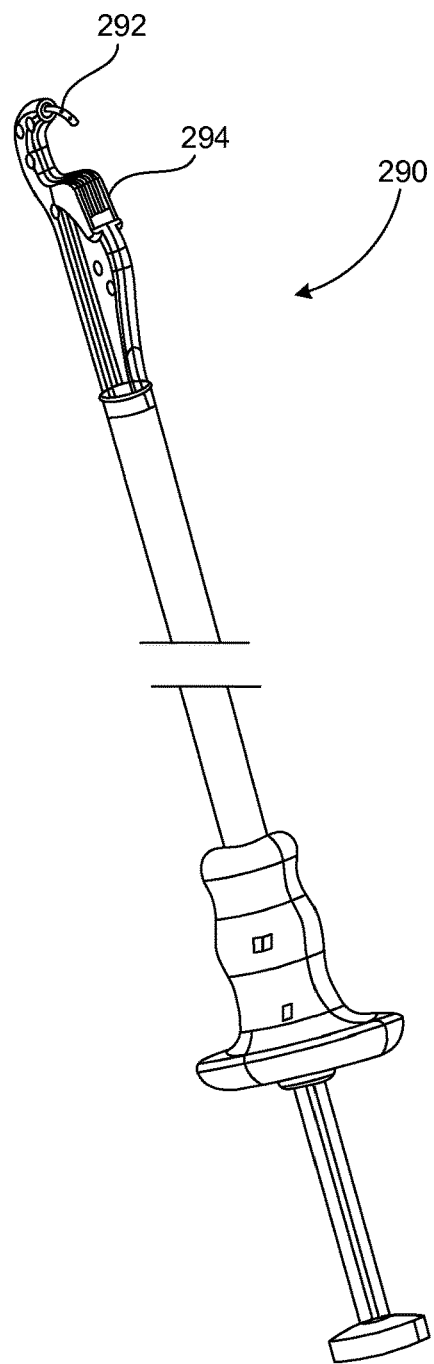
FIG. 4 is a perspective view of an instrument that may be used to deliver the implant of FIGS. 1 and 2 into the body of a patient.

In some embodiments, a delivery assembly is used to facilitate the delivery of the implant into the body of the patient. FIG. 4 is a top view of one of the arm members of the implant 100 or 200 coupled to a delivery assembly 260. The delivery assembly 260 is configured to assist in the implantation and placement of the implant 200 within the body of the patient. Although only one delivery assembly is illustrated, it should be understood that a delivery assembly may be associated with each of the arm members 122 and 126. Additionally, it should be understood that any known delivery assembly and mechanism may be used to deliver and place the implant 200 within the body of the patient.

The delivery assembly includes a sleeve 262 disposed over the first arm member 122. A dilator 264 defining a lumen is coupled to the first sleeve 262 by, for example, crimping, heat sealing, stitching, stretching, tip tipping, etc. Alternatively, the sleeve can be formed to include a portion that forms a tapered dilator. The dilator 264 can be used to expand or enlarge a passage during insertion through bodily tissue, to ease the transition to a cross-section or size of the sleeve 262. In some embodiments, the sleeve 262 is also tapered, which also helps provide a lead-in through the bodily tissue.

The sleeve 262 is secured to the first arm member 122 with a suture 266. The suture 266 is looped through the first arm member 122. In this embodiment, the suture 266 is weaved or threaded through the first arm member 122. For example, as shown in FIG. 4, the suture 266 is weaved through the first arm portion at location A, as well as other locations along the first arm member 122. The threading of the suture 266 through the first arm member 122 can also help prevent stretching of the first arm member 122 during implantation. The strands of the first suture 266 forming the loop through the first arm member 122 extend through an interior lumen (not shown) of the dilator 264 and are crimped closed and heat bonded to an interior wall of the dilator 264 at, for example, a location B shown in FIG. 4, to maintain the first arm member 122 within the sleeve 262 and the dilator 264.

The suture 266 can alternatively be coupled to the first arm member 122 by, for example, crimping, heat sealing, stitching, stretching, tip tipping, etc. In some embodiments, a suture can be threaded to or secured to the first arm portion, for example by knotting.

The suture 266 includes a leader portion 268 that extends distally from the leading end 265 of the dilator 264. Alternatively, a separate suture can be coupled to and extend distally from the dilator. A needle 270 is coupled to a distal end of the leader portion 268 of the first suture 266. The needle 268 can be used to associate the implant 200 to a delivery device, as will be described in more detail below.

The sleeve 262 includes a separator 263 disposed between two strands of the suture 266 and near a distal end of the sleeve 262. The separator 263 maintains separation of the strands of the suture 266 within the sleeve 262. The separation of the strands of the suture 266 enables or helps facilitate a cut to be made through only a single strand of the suture 266 at, for example, location C or D, during removal of the sleeve 262 and the delivery assembly 260, as described in more detail below. In the illustrated embodiment, the separator 263 is a seal, which can be formed, for example, by heat stamping two sides of the sleeve 262 together. Other types of separators can alternatively be used, such as for example, a separate component coupled within the sleeve, or an adhesive can be used to couple the two sides of the sleeve together at a location between the strands.

The dilator 264 tapers from a first diameter at a trailing end 267 to a second, smaller diameter at a leading end 265. The first diameter can be, for example, between about 0.2 and 0.5 cm (0.08 to 0.2 inches) and the second diameter can be, for example, between about 0.03 to 0.2 cm (0.01 to 0.08 inches). For example, in some embodiments, the first diameter can be about 0.37 cm (0.15 inches) and the corresponding second diameter can be 0.03 cm (0.01 inches). The dilator 264 can be formed, for example, by molding, extruding, casting, sintering, forging, machining, or other known methods of manufacturing such medical devices.

In some embodiments, a suturing delivery device 290, as shown in FIG. 4 is used to attach the implant 200 to the bodily tissue. For example, the needle 270 coupled to the first arm member 122 is loaded into the carrier 292 (shown partially extended in FIG. 5) of the delivery device 290. The delivery device 290 can then be used to pass the needle 270 and the first arm member 122 (with the sleeve 262 and the dilator 264 attached thereto) through bodily tissue of the patient, such as the sacrospinous ligament of the patient. Specifically, the carrier 292 of the delivery device 290 is inserted into a body of a patient through the vagina and positioned adjacent the sacrospinous ligament. The carrier 292 is then actuated (for example, by actuating a plunger at an end portion of the delivery device 290) such that the carrier 292 extends and the needle 270 pierces through the sacrospinous ligament. The needle 270 and a distal end of the leader portion 268 of the suture 266 are caught or retrieved by a catch 294 of the delivery device 290 after passing through the sacrospinous ligament. The delivery device 290 is then removed through the vagina, and the needle 270 is removed from the catch 294. The sleeve 262 and the dilator 264 are pulled through the sacrospinous ligament. For example, the user can pull the leader portion 268 of the suture 266 or the dilator 264 through the sacrospinous ligament such that the first arm member 122 is disposed within the sacrospinous ligament. This procedure is then repeated to deliver the second arm portion 226 into the sacrospinous ligament.

After the first arm member 122 and the second arm member 126 are disposed within the sacrospinous ligament, the arm members 122 and 126 can be adjusted to position and tension the body member 110 within the body of the patient. Each arm member 122 and 126 can be delivered sequentially using the same delivery device, or separate delivery devices can be used for some or all of the arm members. The arm members 122 and 126 (with sleeves) can be tensioned using visual guidance as the user observes the positioning of the body member 110 for the correct tension through the vaginal incision.

Figure 3:
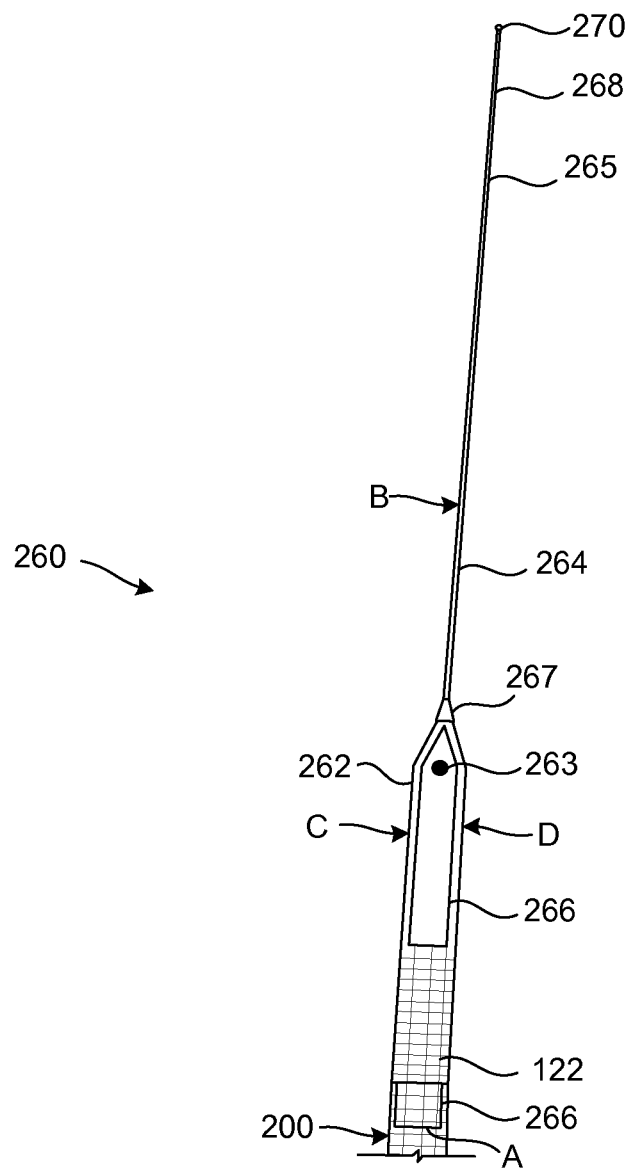
FIG. 3 is a top view of a portion of the implant of FIGS. 1 and 2 coupled to a delivery assembly.

After the arm members 122 and 126 have been placed through the sacrospinous ligament and adjusted as described above, the delivery assemblies can be removed from the arm members 122 and 126. For example, as shown in FIG. 3, to remove the delivery assembly 260 from the arm member 122, a portion of the sleeve 262 and one strand of the loop of the suture 266 within the sleeve 262 can be cut, for example, at location C or D. Because the arm member 122 is coupled to the sleeve 262 via the suture 266, cutting through a portion of the sleeve 262, and one strand of the loop of the suture 266, the sleeve 262 will be freely movable relative to the first arm member 122. The sleeve 262 (and dilator 262 which is coupled to the sleeve 262) can then be pulled off of the first arm member 122 by pulling on the sleeve 262 and the uncut strand of the suture 266. The cut portion of the suture 266 will also be free to pull through the first arm member 122. Thus, the suture 266 remains secured to the sleeve 262 and will simply unravel or unthread itself from the first arm member 122. With the sleeve 262 removed from the first arm member 122, the tangs of the first arm member 122 can engage the surrounding tissue into which the first arm member 122 is placed to couple the first arm member 122 to the bodily tissue (the sacrospinous ligament).

After the arm members 122 and 126 are secured within the sacrospinous ligament, excess portions of the arm members 122 and 126 can be trimmed as needed. For example, if a portion of the first arm member 122 extends through the sacrospinous ligament after the arm members 122 and 126 are placed within the sacrospinous ligament, the portion of the first arm member 122 extending through the sacrospinous ligament can be removed.

Although attachment of the arm members 122 and 126 were described in detail as being inserted into and coupled to the sacrospinous ligament, the arm members 122 and 126 (or additional arm members of the implant) can be secured within a pelvic region (or other portions of the body of the patient) at various different tissue sites. For example, the arm members of the implant can be placed, for example, in a coccygeus muscle. In other embodiments, the arm members are placed through, endopelvic fascia, or through tissue or ligaments near or in the pubococcygeus muscle, puborectalis muscle, distal tendineus arch of levator ani muscle or other tissue locations within a pelvic region. In still other embodiments, the arm members are placed, for example, within an illiococcygeus muscle, or an arcus tendineus.

In some embodiments, a portion of the body member 110 is separately attached to a tissue within the pelvic region. Said another way, a portion of the body member 110 can be secured by means additional to the arm members 122 and 126. For example, a suture can be threaded through the body member 110 and attached to adjacent pelvic tissue, such as the vaginal apex. This can provide additional support for the body member 110.

Figure 5:
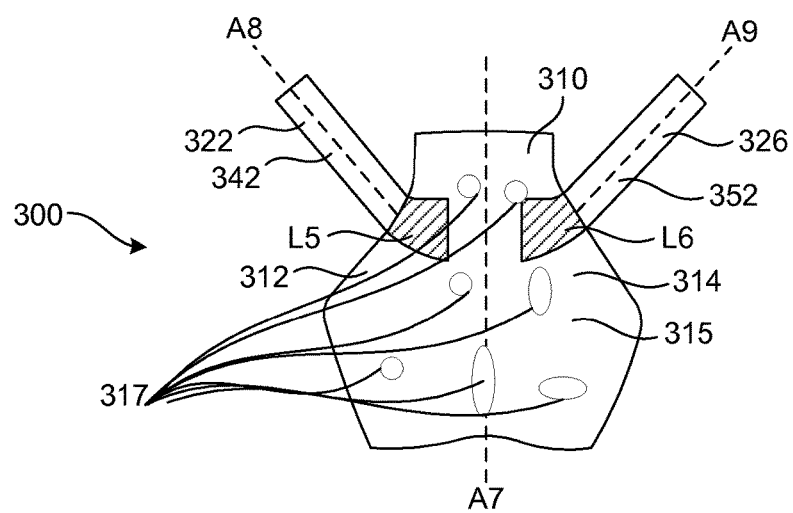
FIG. 5 is a top view of an implant according to an embodiment of the invention.

FIG. 5 is a top view of an implant 300 according to an embodiment. The implant 300 includes a body member 310, a first arm member 322, and a second arm member 326. In this embodiment, the first arm member 322 and the second arm member 326 are not coupled together. Rather each of the first arm member 322 and the second arm member 326 are individually coupled to the body member 310. The implant 300 may include the same or similar features as the implant 100 of FIG. 1 described above.

The body member 310 has a first side portion 312 and a second side portion 314 and defines a longitudinal axis A7. The body member 310 also includes an upper surface 315 and a lower surface (not illustrated) opposite the upper surface 315. In the illustrated embodiment, the body member 310 is formed of an elastic polymer sheet.

The body member 310 includes multiple apertures 317 having different sizes and different shapes. The apertures 317 define properties of the body member 310 including the stiffness and/or elastic properties of the body member 310.

The first arm member 322 may be formed from the same material and the same process as the body member 310. The first arm member 322 extends from the first side portion 312 of the body member 310 along an axis A8 that is non-perpendicular to the longitudinal axis A7 of the body member 310. The first arm member 322 may have and exhibit different properties than the body member 310. In the illustrated embodiment, for example, the first arm member 322 does not include apertures and the first arm member 322 may be stiffer and stronger than the body member 310. In other embodiments, the first arm member 322 may include apertures that have different sizes and/or different shapes than the body member 310. Apertures through the first arm member 322 may enable the first arm member 322 to have different properties than the body member 310.

The first arm member 322 includes an upper surface 342 and a lower surface (not illustrated) opposite the upper surface 342. The first arm member 322 is coupled to the body member 310 such that the lower surface of the first arm member 322 abuts or contacts the upper surface 315 of the body member 310. In the illustrated embodiment, the first arm member 322 is coupled to the body member 310 via stitching at a location L5. In other embodiments, the first arm member 322 is coupled to the body member 310 via another known coupling technique or mechanism.

The second arm member 326 may be formed from the same material and the same process as the body member 310. The second arm member 326 extends from the second side portion 314 of the body member 310 along an axis A9 that is non-perpendicular to the longitudinal axis A7 of the body member 310. Axis A9 is different than axis A8 defined by the first arm member 322 and is non-perpendicular and non-parallel to axis A8. Axis A9 is angled with respect to axis A8.

The second arm member 326 may have and exhibit different properties than the body member 310. In the illustrated embodiment, for example, second arm member 326 does not include apertures and the second arm member 326 may be stiffer and stronger than the body member 310. In other embodiments, the second arm member 326 may include apertures that have different sizes and/or different shapes than the body member 310. Apertures through the second arm member 326 may enable the second arm member 326 to have different properties than the body member 310.

The second arm member 326 includes an upper surface 352 and a lower surface (not illustrated) opposite the upper surface 352. The second arm member 326 is coupled to the body member 310 such that the lower surface of the second arm member 326 abuts or contacts the upper surface 315 of the body member 310. In the illustrated embodiment, the second arm member 326 is coupled to the body member 310 via stitching at a location L6. In other embodiments, the second arm member 326 is coupled to the body member 310 via another known coupling technique or mechanism.

Figure 6:
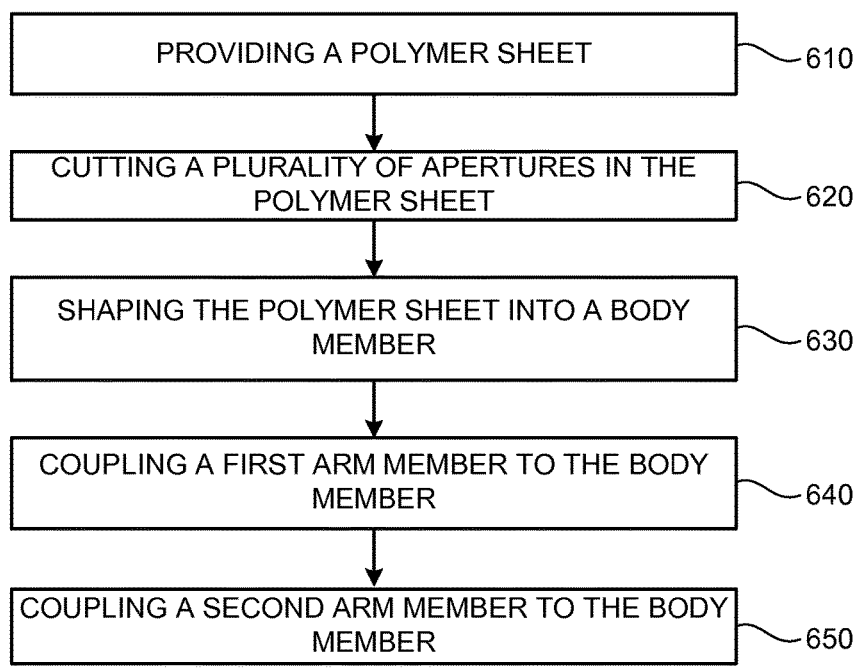
FIG. 6 is a flow chart of a method for making an implant according to an embodiment of the invention.

FIG. 6 is a flow chart of a method for forming an implant according to an embodiment. At step 610 a polymer sheet is provided. In some embodiments, the polymer sheet is provided by extruding the polymer sheet using an extrusion process. In other embodiments, the polymer sheet is provided by molding the polymer sheet using a molding process. In still other embodiments, the polymer sheet is provided by solution casting the polymer sheet using a solution casting process.

At step 620, a plurality of apertures are cut in the polymer sheet. The apertures may be multiple different shapes and/or multiple different sizes. The apertures may be in various locations including located either symmetrically throughout the polymer sheet or asymmetrical throughout the polymer sheet. In one embodiment, the apertures may be laser cut through the polymer sheet. In another embodiment, the apertures may be dye cut through the polymer sheet. The apertures may be used to define the stiffness and/or elastic and/or other properties of the polymer sheet such that the polymer sheet may mimic properties (e.g., stiffness and elastic properties) of bodily tissue, including vaginal tissue and ligaments.

At step 630, the polymer sheet is shaped into a body member of an implant. The body member includes the apertures that were cut into the polymer sheet. The body member includes properties that mimic bodily tissue. The body member may be shaped into different shapes depending on the type of bodily tissue the implant is going to support.

At step 640, a first arm member is coupled to the body member. In some embodiments, the first arm member is coupled to a first side of the body member. At step 650, a second arm member is coupled to the body member. In some embodiments, the second arm member is coupled to a second side of the body member. The first arm member and the second arm member may be from the same polymer sheet or it may be from a different polymer sheet. In other embodiments, the first arm member and the second arm member may be different material than the body member, including being formed from a knitted mesh. The body member may have a first stiffness and the arm members may have a second stiffness, where the second stiffness is more than the first stiffness.

In one embodiment, the arm members may not have any apertures cut through the arm members. In this manner, the stiffness and/or elastic properties may be different from the stiffness and/or elastic properties of the body member.

In other embodiments, the arm members may have apertures that are different sizes and different shapes from the apertures through the body member. In this manner, the stiffness and/or elastic properties may be different from the stiffness and/or elastic properties of the body member.

In one embodiment, an implant includes a body member, a first arm member and a second arm member. The body member is formed of a first material and has a first side portion and a second side portion. The body member has a first stiffness and includes multiple apertures through the body member. The first arm member is formed of a second material and is coupled to and extends from the body member. The second arm member is formed of the second material and is coupled to and extends from the body member. The first arm member and the second arm member have a second stiffness, the second stiffness being more than the first stiffness.

In some embodiments, the plurality of apertures through the body member include at least two different sizes.

In some embodiments, the first arm member is coupled to the first side portion of the body member and extends from the first side portion of the body member. The second arm member is coupled to the second side portion of the body member and extends from the second side portion of the body member.

In some embodiments, the apertures through the body member comprise multiple different sizes.

In some embodiments, the apertures through the body member comprise multiple different shapes.

In some embodiments, the second material is a substantially flat material.

In some embodiments, the first arm member includes a plurality of apertures through the first arm member and the second arm member includes a plurality of apertures through the second arm member. In some embodiments, the apertures through the first arm member and the apertures through the second arm member include multiple different sizes. In some embodiments, the apertures through the first arm member and the apertures through the second arm member include multiple different shapes. In some embodiments, the apertures through the first arm member and the apertures through the second arm member are different in size and shape from the apertures through the body member.

In some embodiments, the first arm member and the second arm member are made from a knitted mesh.

In some embodiments, the first material is different than the second material.

In some embodiments, the first material is made from an elastic polymer.

In some embodiments, the implant is configured to be disposed within a pelvic region of a patient and to provide support to a portion of a body of the patient. In some embodiments, the first arm member and the second arm member are each affixed to a ligament. In some embodiments, the second stiffness is substantially the same as a stiffness of the ligament.

In some embodiments, the first arm member includes a first sleeve and the first sleeve is coupled to the first side portion of the body member. The second arm member includes a second sleeve and the second sleeve is coupled to the second side portion of the body member.

In one embodiment, a method of forming an implant includes providing a polymer sheet, cutting a plurality of apertures in the polymer sheet and shaping the polymer sheet into a body member. The body member has a first stiffness and is to be disposed within a body of a patient and to provide support for a portion of the body of the patient. The method includes coupling a first arm member to the body member and coupling a second arm member to the body member, where the first arm member and the second arm member have a second stiffness and the second stiffness is more than the first stiffness.

In some embodiments, coupling the first arm member to the body member includes coupling the first arm member to a first side portion of the body member and coupling the second arm member to the body member includes coupling the second arm member to a second side portion of the body member.

In some embodiments, providing the polymer sheet includes extruding the polymer sheet.

In some embodiments, providing the polymer sheet includes molding the polymer sheet.

In some embodiments, providing the polymer sheet includes solution casting the polymer sheet.

In some embodiments, cutting the plurality of apertures in the polymer sheet includes laser cutting the plurality of apertures in the polymer sheet, where the apertures have a plurality of different sizes and a plurality of different shapes.

In some embodiments, cutting the plurality of apertures in the polymer sheet includes dye cutting the plurality of apertures in the polymer sheet, where the apertures have a plurality of different sizes and a plurality of different shapes.

In some embodiments, the method includes cutting a plurality of apertures through the first arm member and the second arm member, where the apertures through the first arm member and the second arm member have different sizes and different shapes from the apertures through body member.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implant, comprising:
a body member formed of a first elastic polymer sheet and having a first side portion, a second side portion, a first surface and a second surface opposite to the first surface, the first elastic polymer sheet including a non-mesh material that defines a plurality of apertures such that the body member has a first stiffness substantially similar to a stiffness of bodily tissue, the plurality of apertures being of different sizes and shapes and irregularly spaced apart;
a first arm member formed of a second elastic polymer sheet including a non-mesh material, the first arm member includes a plurality of apertures, the plurality of apertures of the first arm member being of different sizes and shapes and irregularly spaced apart, the first arm member having an end portion, the end portion overlapping with the first surface at the first side portion of the body member, the overlapping portion being stitched to the first surface, wherein a remaining portion of the first arm member is non-stitched, the remaining portion extending from an edge of the body member to a terminal end of the first arm member, the remaining portion being linear, the overlapping portion being disposed at a non-zero angle with respect to the remaining portion, the first arm member defining a second stiffness that is greater than the first stiffness of the body member; and
a second arm member formed of a third elastic polymer sheet including a non-mesh material, the second arm member being coupled to and extending from the body member, the second arm member defining a third stiffness that is greater than the first stiffness of the body member.

2. The implant of claim 1, wherein the second arm member is coupled to the second side portion of the body member and extends from the second side portion of the body member.

3. The implant of claim 1, wherein the plurality of apertures of the body member include apertures that penetrate through the first elastic polymer sheet and apertures that do not penetrate through the first elastic polymer sheet.

4. The implant of claim 1, wherein:
the third elastic polymer sheet of the second arm member defines a plurality of apertures through the third elastic polymer sheet of the second arm member.

5. The implant of claim 4, wherein the apertures through the second elastic polymer sheet of the first arm member and the apertures through the third elastic polymer sheet of the second arm member are different in size and shape from the apertures defined by the body member.

6. The implant of claim 1, wherein a portion of the second elastic polymer sheet and a portion of the third elastic polymer sheet are devoid of apertures.

7. The implant of claim 1, wherein the second arm member includes an end portion, the end portion of the second arm member overlapping with the first surface at the second side portion of the body member, the overlapping portion of the second arm member being stitched to the first surface.

8. The implant of claim 1, wherein the body member is configured to be coupled to vaginal tissue, and the first arm member and the second arm member are each configured to be affixed to a ligament.

9. The implant of claim 8, wherein the second stiffness and the third stiffness are substantially the same as a stiffness of the ligament.

10. The implant of claim 1, wherein:
the first arm member comprises a first sleeve, the first sleeve being coupled to the first side portion of the body member; and
the second arm member comprises a second sleeve, the second sleeve being coupled to the second side portion of the body member.

11. A method of forming an implant, comprising:
providing a first elastic polymer sheet having a non-mesh material;
cutting a plurality of apertures in the first elastic polymer sheet, the plurality of apertures being of different sizes and shapes and irregularly spaced apart;
shaping the first elastic polymer sheet into a body member, the body member having a first stiffness and to be disposed within a body of a patient and to provide support for vaginal tissue within the body of the patient, the first stiffness being substantially similar to a stiffness of the vaginal bodily tissue, the body member having a first side portion, a second side portion, a first surface, and a second surface opposite to the first surface;
coupling a first arm member to the body member, the first arm member includes a plurality of apertures, the plurality of apertures of the first arm member being of different sizes and shapes and irregularly spaced apart, the first arm member being formed of a second elastic polymer sheet including a non-mesh material, the first arm member having a second stiffness that is greater than the first stiffness, the first arm member having an end portion, the end portion overlapping with the first surface at the first side portion of the body member, wherein the coupling includes stitching the overlapping portion to the first surface, wherein a remaining portion of the first arm member is non-stitched, the remaining portion extending from an edge of the body member to a terminal end of the first arm member, the remaining portion being linear, the overlapping portion being disposed at a non-zero angle with respect to the remaining portion; and coupling a second arm member to the body member, the second arm member being formed of a third elastic polymer sheet including a non-mesh material, the second arm member having a third stiffness that is greater than the first stiffness.

12. The method of claim 11, wherein the coupling of the second arm member to the body member includes coupling the second arm member to the first surface of the body member such that the second arm member overlays with the first surface at the second side portion of the body member.

13. The method of claim 11, wherein the cutting includes laser cutting the apertures through the first elastic polymer sheet.

14. The method of claim 11, wherein the cutting includes die cutting the apertures through the first elastic polymer sheet.

15. The method of claim 11, further comprising:
cutting a plurality of apertures through the second elastic polymer sheet; and
cutting a plurality of apertures through the third elastic polymer sheet.

* * * * *